US012162786B2

(12) United States Patent
Casad, Jr.

(10) Patent No.: US 12,162,786 B2
(45) Date of Patent: Dec. 10, 2024

(54) METHODS FOR VALORIZATION OF LIGNIN-RICH SOLIDS FROM ANAEROBIC DIGESTATE

(71) Applicant: Robert C. Casad, Jr., Frederiksberg (DK)

(72) Inventor: Robert C. Casad, Jr., Frederiksberg (DK)

( * ) Notice: Subject to any disclaimer, the term of this patent is extended or adjusted under 35 U.S.C. 154(b) by 0 days.

(21) Appl. No.: 17/781,751

(22) PCT Filed: Dec. 2, 2020

(86) PCT No.: PCT/US2020/062763
§ 371 (c)(1),
(2) Date: Jun. 2, 2022

(87) PCT Pub. No.: WO2021/145968
PCT Pub. Date: Jul. 22, 2021

(65) Prior Publication Data
US 2023/0357065 A1    Nov. 9, 2023

(51) Int. Cl.
*A01C 3/00* (2006.01)
*C02F 11/04* (2006.01)
(Continued)

(52) U.S. Cl.
CPC .............. *C02F 11/04* (2013.01); *A01C 3/00* (2013.01); *C02F 11/12* (2013.01); *C02F 11/127* (2013.01)

(58) Field of Classification Search
CPC .. C02F 11/04; C02F 3/28; C02F 11/12; C02F 11/121; C02F 11/127; C02F 11/14;
(Continued)

(56) References Cited

U.S. PATENT DOCUMENTS

| 4,526,791 A | * | 7/1985 | Young | ................... C12N 1/22 |
| | | | | 435/911 |
| 11,168,339 B1 | * | 11/2021 | Stepany | ................ C12P 5/023 |

(Continued)

FOREIGN PATENT DOCUMENTS

| RU | 2271347 C2 | * | 3/2006 |
| RU | 2680682 C1 | * | 2/2019 |

OTHER PUBLICATIONS

English Translation of Patent Publication RU 2271347, published Mar. 10, 2006 (Year: 2006).*

(Continued)

*Primary Examiner* — Joseph W Drodge (57) ABSTRACT

A liquid suspension of lignin-rich microparticles can be recovered from anaerobic digestion of ruminant animal manure. This has similar particle size distribution to that obtained from anaerobic digestion of steam pretreated lignocellulosic feedstocks. This demonstrates that similar lignin-rich microparticles can also be formed biologically, in the absence of thermal treatment that melts lignin. As a consequence, given a sufficiently complete digestion, lignin-rich microparticles will be formed during anaerobic digestion of ruminant manure and of lignocellulosic feedstocks that have never been steam pretreated to temperatures above the lignin melting point. Methods for recovering and valorizing this lignin are disclosed.

16 Claims, 5 Drawing Sheets

Particle size distribution for suspended solids in cow manure digestate liquid fraction (1) and in steam pretreated wheat straw digestate liquid fraction (2).

(51) Int. Cl.
  *C02F 11/12*  (2019.01)
  *C02F 11/127*  (2019.01)
(58) Field of Classification Search
  CPC .... C02F 11/143; C02F 2103/20; Y02E 50/30;
       C12P 5/023; C12P 19/02; C12P 2201/00;
       C05F 3/00; C05F 3/06; A01C 3/00; A23K
                  10/20; A23K 10/26
  USPC .......................................................... 71/21
  See application file for complete search history.

(56) References Cited

U.S. PATENT DOCUMENTS

| | | | | |
|---|---|---|---|---|
| 2002/0114866 | A1* | 8/2002 | Kartchner | A23K 30/20 |
| | | | | 426/55 |
| 2014/0142353 | A1* | 5/2014 | Hitzl | C10G 1/02 |
| | | | | 422/111 |
| 2015/0005482 | A1* | 1/2015 | Roa-Espinosa | C02F 1/56 |
| | | | | 530/421 |
| 2017/0152199 | A1* | 6/2017 | Feghali | C08H 6/00 |
| 2019/0203012 | A1* | 7/2019 | Shi | C08J 11/16 |
| 2019/0309472 | A1* | 10/2019 | Casad, Jr. | D21B 1/30 |

OTHER PUBLICATIONS

English Translation of Patent Publication RU 2680682C1, published Feb. 25, 2019. (Year: 2019).*

* cited by examiner

Figure 1. Particle size distribution for suspended solids in cow manure digestate liquid fraction (1) and in steam pretreated wheat straw digestate liquid fraction (2).

Figure 2. Calculated molecular weight distribution for lignin microparticles recovered from digestate of steam pretreated wheat straw (1) and cow manure (2, 3, 4, 5).

METHODS FOR VALORIZATION OF LIGNIN-RICH SOLIDS FROM ANAEROBIC DIGESTATE

This application claims priority to U.S. provisional patent applications 62/942,215, filed Dec. 2, 2019, and 63/087,173, filed Oct. 2, 2020, each of which is hereby incorporated by reference in entirety.

WO2020/033633, which is hereby incorporated by reference in entirety, teaches that residual lignin in digestate from homogeneous anaerobic digestion of wheat straw pellets steam pretreated so as to avoid agitation as described in WO2018/085487 exists primarily as comparatively pure microparticles with diameters on the order <3 μm.

These lignin microparticles can be readily separated from fibers and other suspended solids and recovered directly as a liquid suspension.

The previously reported lignin microparticles correspond to small globules of lignin which melted and subsequently re-condensed during hydrothermal pretreatment. The formation of these microdroplets is a general phenomenon in hydrothermal pretreatment of lignocellulosic biomass, see Li (2014), which has been observed experimentally in at least wood chips, shrubberies, switchgrass, wheat and corn straw. See Selig (2007), Donohoe (2008), Xiao (2011), Hansen (2013), Pu (2013), Ji (2016).

Here we report that, very surprisingly, a liquid suspension of lignin-rich microparticles can be recovered from cow manure digestate that has similar particle size distribution to that obtained from anaerobic digestion of steam pretreated lignocellulosic feedstocks. This demonstrates that similar lignin-rich microparticles can also be formed biologically, in the absence of thermal treatment that melts lignin. As a consequence, given a sufficiently complete digestion, similar lignin-rich microparticles will be formed during anaerobic digestion of ruminant manure and, under appropriate conditions, even from lignocellulosic feedstocks that have never been steam pretreated to temperatures above the lignin melting point.

DESCRIPTION OF EMBODIMENTS

Digestate from centralized anaerobic digestion of ruminant animal manure comprises a large proportion of lignin, typically between 30-35% of total volatile solids. See Machtig (2020). Our studies with digestate from a commercial Danish biogas plant in which approximately 85% of the input feed dry matter (DM) is from cow manure show that most of the lignin content consists of suspended lignin microparticles which are very similar to those observed previously in digestate from homogeneous anaerobic digestion of steam pretreated wheat straw pellets, as described in WO2020/033633.

The cow manure digestate was separated by screw press into a solid fraction and a liquid fraction having volume fraction approximately ⅓ (solid fraction including associated liquid) and ⅔ liquid fraction. The screw press liquid fraction was further subject to simulated decanter centrifugation (5 minutes at 3600 g in a table top centrifuge) to provide "cow manure digestate simulated decanter liquid fraction." When pH of this simulated decanter liquid fraction is adjusted to <2, the material behaves exactly like simulated decanter liquid fraction from digestate of steam pretreated wheat straw pellets. See FIG. 1, which shows the appearance of cow manure digestate simulated decanter liquid fraction after adjustment to pH<2 followed by additional simulated decanter centrifugation, and FIG. 2, which shows supernatant from simulated decanter centrifugation of cow manure digestate liquid fraction for control (pH 8, unadjusted, black color) and after adjustment to pH<2 (yellow color, N=2). As shown, suspended particles which give the cow manure digestate liquid fraction a dark black appearance flocculate and readily precipitate, leaving behind a yellow colored supernatant, exactly as reported previously for steam pretreated wheat straw digestate liquid fraction.

The particle size distribution of suspended microparticles in cow manure digestate simulated decanter liquid fraction is strikingly similar to that observed in simulated decanter liquid fraction from digestate of steam pretreated wheat straw pellets. See FIG. 3, which shows the particle size distribution determined by Zeta Sizer™ dynamic light scattering (Malvern) for suspended solids in cow manure digestate liquid fraction at 1:700 dilution (green trace; light) and for steam pretreated wheat straw digestate liquid fraction after microfiltration at 1:770 dilution (red trace; dark). As shown, digestate liquid fraction from both cow manure and steam pretreated wheat straw have a sharp peak centered around about 4000 nm in diameter, as determined in this experimental system. Both have a similar broad peak centered around a smaller size—about 1200 nm in the case of cow manure digestate liquid fraction, compared with about 900 nm in the case of steam pretreated wheat straw digestate. The steam pretreated wheat straw digestate exhibits an additional peak not observed in cow manure digestate which is centered around a still smaller size of about 30 nm.

The suspended solids in cow manure digestate liquid fraction exhibit UV absorbance that is consistent with lignin content. See FIG. 4, which shows the UV absorbance spectrum (190-400 nm) of a lignosulfonate standard (control+) and cow manure digestate liquid fraction adjusted to NaOH content 4 wt. % at several dilutions (circles 1:1000, squares 1:500, triangles 1:100). As shown, the NaOH-solubilized cow manure digestate liquid fraction solids exhibit UV absorbance similar to that of lignosulfonate standard. That the suspension of liquid microparticles recovered from simulated decanter centrifugtion of cow manure digestate indeed comprises lignin was confirmed by Klason lignin analysis performed by Celignis Laboratories, Limerick—lignin content comprised 58% of volatile solids in a sample of digestate simulated decanter liquid fraction. Based on the assumption that approximately 30% of the initial VS in the digestate sample before any solid liquid separation was lignin, the total recovery of lignin content in simulated decanter liquid fraction was >70%.

The molecular weight distribution of NaOH-soluble material in suspended microparticles from digestate of steam pretreated wheat straw pellets, which were previously shown to comprise about 80 wt. % lignin, is strikingly similar to that observed in suspended microparticles from cow manure digestate. See FIG. 5, which shows the calculated molecular weight distribution determined by A280 elution profile in size exclusion HPLC at 0.1 N NaOH compared against polyethylene glycol standards. The overlay of curves at the peak corresponding to molecular weight about 600 shows sample 5 uppermost, followed by sample 3, then sample 1, then sample 4, then sample 2 lowermost. Sample 1 is from lignin microparticles recovered from steam pretreated wheat straw digestate simulated decanter liquid fraction by flocculation at pH<2 with subsequent isolation, concentration and dissolution in 7.3 wt. % KOH. Samples 2 and 4 are from cow manure digestate simulated decanter liquid fraction with NaOH added to 4 wt. % at different dilutions. Samples 3 and 5 are from NaOH extract from cow manure digestate screw press solid fraction at different dilutions. The molecular weight distribution of NaOH-soluble material from suspended microparticles from cow manure digestate simulated decanter liquid fraction (samples 2 and 4) appears virtually identical to that obtained from NaOH extract of cow manure digestate solid fraction (samples 3 and 5). The curves for cow manure digestate samples 3 and 5, having greater A280 intensity simply because of differences in dilution, clearly show a striking similarity with NaOH-soluble material from wheat straw digestate lignin microparticles sample 1.

These results demonstrate that lignin microparticles can be formed from lignocellulosic biomass during anaerobic digestion without any requirement that lignin be melted. Biological processing alone, such as occurs in ruminant digestion or in the qualitatively similar process in anaerobic digestion, is apparently sufficient to transform undigestible native lignin content into a distribution of suspended microparticles having particles sizes very similar to those obtained where lignin is melted into tiny globules during steam pretreatment.

Without wishing to be bound by theory, the formation of suspended microlignin particles by biological process appears to occur according to a similar mechanism as that which produces microlignin globules by melting. The mechanisms of lignin self-association are undoubtedly complex, either as dissolved solids or as hydrophobic aggregates of undissolved solids. See e.g. Mishra (2019) for review. Nevertheless, it is reasonable to speculate that the size of lignin aggregates in an aqueous environment might ultimately be limited by electrostatic repulsion between particles. That is to say, any tendency for "ripening" of aggregate microparticles into larger particles could be expected to be counter-acted by electrostatic repulsion where the particle surface is negatively charged at the pH conditions of anaerobic digestion (>6). Native lignin is known to comprise some quantity of carboxylic acid substituents. See e.g. Pu (2011) and Guerra (2006). For example, Pu (2011) reports the native carboxylic acid content of switchgrass lignin as 0.29 mmol/g. This corresponds to an incidence of carboxylic acid groups of about 1 for every 19 lignin monomers. In this case, a lignin molecule having molecular weight about 3400 would be expected to have one carboxylic acid group, which would be negatively charged at pH>4, to the extent that it was exposed to aqueous solvent. As lignocellulosic biomass is consumed during ruminant digestion or controlled anaerobic digestion, surrounding carbohydrate content is enzymatically hydrolysed according to molecular mechanisms that leave insoluble lignin molecules exposed to an aqueous environment. The lignin molecules will, in these circumstances, aggregate. Although nothing is yet known about the conformation of lignin molecules in aggregates, it is reasonable to assume that it is compressed, leaving an interior milieu with reduced dielectric properties relative to water. Negative charged groups in the interior of lignin aggregates could be expected to be minimized. Carboxylic acid groups might well remain neutral in these conditions. On the growing microparticle (aggregate) surface, however, charged groups exposed to solvent could be expected to be enriched. The conformation of lignin molecules at the particle surface could be expected to maximize solvent exposure of the negatively charged carboxyl groups. To the extent that lignin aggregate size is ultimately limited by surface charge, a greater incidence of carboxylic acid content could be expected to be associated with a smaller particle size. That there exists, in both steam pretreated wheat straw digestate and also in cow manure digestate, a more-or-less bimodal distribution of similarly small particle sizes is consistent with an underlying heterogeneity of carboxylic acid content, meaning some lignins may have more or less carboxylic acid content than others, within the same native feedstock.

It is notable that, notwithstanding the well known tendency for Kraft lignin to self-associate in solution, the liquid suspension of lignin microparticles obtained from digestate is quite stable in that no sedimentation is observed even after many months of storage at 4° C.

In some embodiments, the invention provides a method for valorization of lignin-rich solids from anaerobic digestate comprising the steps of:
  conducting anaerobic digestion on an input feed in which the predominant component is ruminant animal manure or a combination of lignocellulosic biomass and ruminant animal manure;
  processing digestate from said anaerobic digestion so as to produce at least one solid fraction and at least one liquid fraction which liquid fraction comprises suspended lignin-rich microparticles;
  processing the at least one liquid fraction comprising suspended lignin-rich microparticles so as to precipitate the suspended lignin-rich microparticles or so as to increase the concentration of suspended lignin-rich microparticles to at least 24 g/L, or so as to dissolve the lignin content of the suspended lignin-rich microparticles in hydroxide solution, and
  processing the precipitated lignin microparticles or the concentrated liquid suspension or lignin hydroxide solution so as to valorize the lignin content, wherein the lignocellulosic biomass has not been hydrothermally pretreated at temperature 130° C. or higher.

In some embodiments, the invention provides a method for valorization of lignin from anaerobic digestate comprising the steps of:
  conducting anaerobic digestion on an input feed in which the predominant component is ruminant animal manure or a combination of lignocellulosic biomass and ruminant animal manure;
  processing digestate from said anaerobic digestion by adding hydroxide base sufficient to dissolve lignin content of suspended lignin microparticles and also solubilize some lignin content within larger fibers and other suspended solids to form a lignin hydroxide solution, processing hydroxide base treated digestate from said anaerobic digestion so as to produce at least one solid fraction and at least one liquid fraction comprising dissolved lignin, and processing the at least one liquid fraction so as to valorize its lignin content, optionally further processing the at least one solid fraction in subsequent additional anaerobic digestion.

Hydroxide solution refers to a solution comprising hydroxide base and is normally made using sodium or potassium hydroxide, but can also be made using calcium hydroxide at its limit of solubility.

One skilled in the art will readily understand that any convenient method of anaerobic digestion known in the art may be applied using ruminant animal manure in any form, optionally with a co-feed of litter material, silage, grass or other lignocellulosic material. It is generally advantageous to conduct anaerobic digestion as a "wet" process where total solids is between 0.1 and 17% by weight.

As explained previously in WO2020/033633, any convenient means of solid liquid separation may be applied, including both centrifugal and non-centrifugal means. In some embodiments, digestate is subject to decanter centrifugation and the solid fraction washed to recover additional lignin-rich microparticles that are trapped in the pellet. In some embodiments, a screw press is applied to provide an initial solid/liquid separation followed by one or more screening of filtration steps to remove larger suspended solids, providing a liquid fraction comprising suspended lignin-rich microparticles from which other suspended solids have been substantially removed. One skilled in the art will readily determine, without undue experimentation, an appropriate method of solid/liquid separation that provides a suitable liquid fraction comprising suspended lignin-rich microparticles. In some embodiments, at least 50% by weight of volatile solids content of a suitable liquid fraction is lignin content, or at least 40%, or at least 60%, or between 40 and 99%, or between 60 and 85%. In some embodiments, the concentration of suspended lignin-rich microparticles in the at least one liquid fraction is initially at least 3 g DM/L, or at least 4 g/L, or at least 5 g/L or at least 6 g/L or at least 7 g/L or at least 10 g/L or at least 20 g/L or at least 30 g/L or at least 40 g/L or between 3 and 80 g/L. In some embodiments, the concentration of lignin content is increased to at least 24 g/L, or at least 30 g/L, or at least 40 g/L, or at least 50 g/L, or between 24 and 300 g/L. As used herein the "concentration of lignin content" is distinct from the "concentration of lignin rich microparticles" and refers to the concentration of Klason lignin. As will be readily understood by one skilled in the art, where a suspension of lignin-rich microparticles has concentration at least 40 g/L of which lignin content is at least 60% by weight, the "concentration of lignin content" will be at least 24 g/L.

In some embodiments, sodium or potassium hydroxide or calcium hydroxide at its limit of solubility sufficient to dissolve lignin content is added directly to liquid fraction comprising suspended lignin-rich microparticles so as to dissolve the lignin content. Alternatively, hydroxide base sufficient to dissolve lignin content can be added directly to whole digestate prior to any solid liquid separation with solid/liquid separation applied only after base addition. The resulting lignin solutions can then be concentrated using membrane processes and related methods well known in the art that are routinely applied to concentrate Kraft black liquour solutions in pulp and paper processing. In some embodiments, such resulting lignin hydroxide solutions are concentrated to a lignin content of at least 24 g/L, or at least 30 g/L, or at least 40 g/L, or at least 50 g/L, or between 24 and 300 g/L. In order to solubilize "native" lignin content in manure digestate, a concentration of at least 0.1 M NaOH or KOH is typically sufficient. Calcium hydroxide at its limit of solubility is also able to dissolve some lignin. In some embodiments, after addition of hydroxide base, stirring and gentle heating to between 40 to 70° C. can enhance lignin solubilization. In some embodiments, an even lower concentration of NaOH or KOH may be applied to conserve process costs, although this is typically associated with a reduced solubilization. In some embodiments concentrations as low as 50 mM or 70 mM or between 40 mM and 100 mM NaOH or KOH can be applied. In some embodiments, calcium hydroxide may be used at the limit of solubility.

In some embodiments, the weight percentage of suspended lignin microparticles in liquid fraction can be increased by concentration using any means known in the art, with optional subsequent addition of sodium or potassium hydroxide and further concentration of solubilized lignin content. Typically manure digestate liquid fraction will have total solids between 2-7 wt. % Commercially practicable filtration systems including but not limited to cross-flow filtration systems can readily increase the concentration of lignin-rich microparticles to at least 10 wt. % while retaining the suspension of microparticles in pumpable liquid form. In some embodiments, the concentration of suspended lignin-rich microparticles in the at least one liquid fraction is increased from its initial concentration to at least 10 g/L or at least 20 g/L or at least 24 g/L or at least 30 g/L or at least 40 g/L or between 3 and 80 g/L or between 10 and 120 g/L, or between 40 and 110 g/L. In some embodiments, lignin content of suspended lignin microparticles can be dissolved in hydroxide solution after an initial step to increase the concentration of suspended lignin microparticles. As will be readily understood by one skilled in the art, this can help reduce consumption of hydroxide base. In some embodiments, lignin content of suspended lignin microparticles can be directly dissolved by adding hydroxide base to the liquid fraction. In some embodiments, the lignin content dissolved in hydroxide solution can be further concentrated to between 24 and 300 g/L.

In some embodiments, the suspended lignin microparticles can be flocculated and precipitated by any suitable means known in the art, including any of the methods described in WO2020/033633. Typically pH is lowered to <4, or <3, or <2 or between 1 and 3 followed by either passive sedimentation or filtatration. In some embodiments, the lignin content of lignin-rich microparticles sediment or filter cake is dissolved by addition of hydroxide base to form a lignin hydroxide solution.

The precipitated lignin or liquid suspension of lignin-rich microparticles can be valorized by a variety of means known in the art. In some embodiments, a liquid suspension may be used for catalytic thermal treatments using surface catalysts or other catalysts to produce higher value chemicals. In some embodiments, this suspension may be used to create a solution in which lignin is dissolved, for example by adding sodium or potassium hydroxide as explained above. Lignin hydroxide solutions can then be used for further processing such as catalytic depolymerization, mild oxidation to produce cement plasticizers, or formation of resins according to process known in the art. In some embodiments, hydroxide solutions of recovered lignin can be used in high solids alkaline oxidation as described in U.S. 62/984,302, for example, to produce water soluble oxidation products that can be used for subsequent digestion to produce additional biomethane. Applying the average estimated methane yield from anaerobic digestion of cow manure in continuous stirred tank (CSTR) systems of 190 Nm$^3$/ton VS reported in a literature meta-analysis by Miranda (2016), and an estimated yield from lignin oxidation products corresponding to 509 Nm$^3$/ton intial lignin VS described in U.S. 62/984,302, biomethane conversion of undigested lignin recovered as described here could increase yields from cow manure on the order of 39%. In some embodiments, precipitated lignin may be dissolved in hydroxide solution and used for In some embodiments, instead of processing the at least one liquid fraction so as to increase the concentration of lignin-rich microparticles in liquid suspension, hydroxide base can be added directly to dissolve lignin content. The dissolved lignin content in such solutions can then be concentrated using means known in the art to concentrate Kraft lignin in black liquor or using other means known in the art.

In some embodiments, instead of processing digestate from said anaerobic digestion so as to produce at least one solid fraction and at least one liquid fraction which liquid fraction comprises suspended lignin-rich microparticles, hydroxide base can be added directly to whole digestate so as to dissolve lignin content of suspended lignin microparticles and also solublize lignin content within larger suspended solids (such as fibers), which would normally be separated by solid/liquid separation. The pH-adjusted digestate can then be further processed using means known in the art to achieve solid liquid separation. The base-treated solids recovered after solid/liquid separation can be expected to have residual biomethane potential that could be fruitfully realized in subsequent digestion. The dissolved lignin content in such solutions can then be concentrated using means known in the art to concentrate Kraft lignin in black liquor or using other means known in the art.

As used here, the "lignocellulosic biomass has not been hydrothermally pretreated at temperature 130° C. or higher" to the extent that <20% by weight of lignocellulosic biomass DM applied in the digestion has been hydrothermally pretreated as described.

The term "suspended lignin-rich microparticles" as used here has the same meaning as that given in WO2020/033633: "Suspended microparticles" refers to suspended particles that pass through a WHATMAN™ grade 4 filter paper (pore size 20 to 25 µm) under circumstances in which the filter paper is not fouled by accumulated solids. "Concentration of suspended lignin-rich microparticles at least X g dry matter (DM)/L" refers to a measurement made as follows: DM content of the at least one liquid fraction in which the measurement is to be made is determined by drying at 105° C. The liquid fraction is then diluted so that DM content is 10 g/L and 100 ml of the diluted liquid fraction passed by gravity and without vacuum suction through a WHATMAN™ grade 4 filter paper (pore size 20 to 25 µm), stirring if necessary to avoid filter fouling. Volume of dilute filtrate is noted and DM content determined by drying at 105° C. Filtrate is subject to centrifugation 3 hours at 30.000 g to precipitate suspended solids. DM content of the centrifuge supernatant is determined by drying at 105° C. The difference between DM concentration in filtrate and DM concentration in centrifuge supernatant is concentration of suspended microparticles. To the extent that (observed concentration of suspended microparticles in g/L) *(dilution factor applied to liquid fraction) is at least X g/L, the concentration of suspended microparticles in liquid fraction is at least X g DM/L. Composition of the suspended microparticles is determined using washed filter cake obtained from a sample prepared by adjusting pH of the at least one liquid fraction to 2.0 followed by filtration using a 20 µm filter with applied vacuum suction to produce a filter cake which is then resuspended in 4 volumes of water at pH 2.0 then filtered again with applied vacuum suction to produce a second filter cake with washing repeated twice to produce a fourth filter cake. Ash, carbohydrate, and lignin content of the fourth filter cake is determined as described in "Determination of structural carbohydrates and lignin in biomass," Laboratory Analytical Procedure issue date April 2008 US National Renewable Energy Laboratory Technical Report NREL/TP-510-42618 revised August 2012, except that all calculations are made without correction for extractives and except that acid soluble lignin content is determined using 205 nm absorptivity of 110 L/g cm and except that equivalent reagents and laboratory equipment to that specifically named by brand may be used. "Lignin-rich" refers to composition in which >60% wt. % of the non-ash content is lignin, where ash, carbohydrate, and lignin content is determined as described above. As used herein "lignin content" refers to Klason lignin content determined as described above.

EXAMPLES

1. Solid Liquid Separation of Digestate and Estimation of Lignin Recovery.

A sample of digestate liquid fraction (about 2 liters) was obtained from BlUbjerg Biogas, Nørre Nebel, Denmark. The input feed to the digestion comprised approximately 85% cow manure. The digestate was processed on-site by screw press to produce a solid fraction and a liquid fraction. A 430 ml sample of this liquid fraction was further subject to simulated decanter centrifugation at Lund University Department of Chemical Engineering by centrifugation 5 minutes at 3600 g using a table top centrifuge. Based on the DM of the recovered centrifuge pellet and supernatant (determined by drying at 105° C. as means of duplicate samples), in the sample tested, the pellet included 8.0 g actual precipitated pellet DM as well as 0.8 g "trapped" supernatant DM. Pellet volume was approximately 44 ml. In this case, 47% of DM was precipitated by simulated decanter centrifugation while 53% remained in liquid suspension. Total DM of a sample of this simulated decanter supernatant was analysed at Celignis Laboratories, Limerick, Ireland, and determined to be 59.7% volatile solids (VS), of which 58.0% was Klason lignin. Where the digestate screw press solids fraction contained an estimated 40% of total DM, lignin recovery in simulated decanter supernatant can be roughly estimated as follows: Total initial VS was 35.4 g/L of which 30% is assumed to be lignin, extrapolating from results reported by Machtig (2019), for an estimated 100% theoretical yield of 10.6 g/L lignin. The lignin content of suspended solids in simulated decanter liquid fraction was 8.2 g/L which is corrected for loss of pellet volume to 7.7 g/L, corresponding to about 72.6% of theoretical. The remaining lignin content is presumed to be contained within the screw press solids and simulated decanter pellet. The simulated decanter liquid fraction from cow manure was dark black, having very similar appearance as the simulated decanter liquid fraction from digestate of steam pretreated wheat straw pellets described in example 1 and shown in FIG. 2 of WO2020/033633.

2. Concentration of Suspended Lignin Microparticles by Ultrafiltration.

The simulated decanter liquid fraction referred to in example 1 was concentrated using ultrafiltration in a stirred pressure cell fitted with a membrane having nominal exclusion 100 Kd. Ultrafiltration was conducted at 2 bar nitrogen pressure. The retentate had total solids 6.95 wt. % (mean of duplicates). Approximately 50% of the suspended solids passed through the membrane and were recovered as filtrate. A similar simulated decanter liquid fraction was obtained from a stored sample of frozen digestate recovered from anaerobic digestion of steam pretreated wheat straw pellets as described in WO2020/033633. The wheat straw liquid fraction was similarly concentrated as described for cow manure digestate liquid fraction to final DM 11.23% (mean of duplicates). The concentrated wheat straw suspension remained liquid and was apparently "pumpable" even at this high concentration.

3. Particle Size Determination of Suspended Solids.

Figure 3:
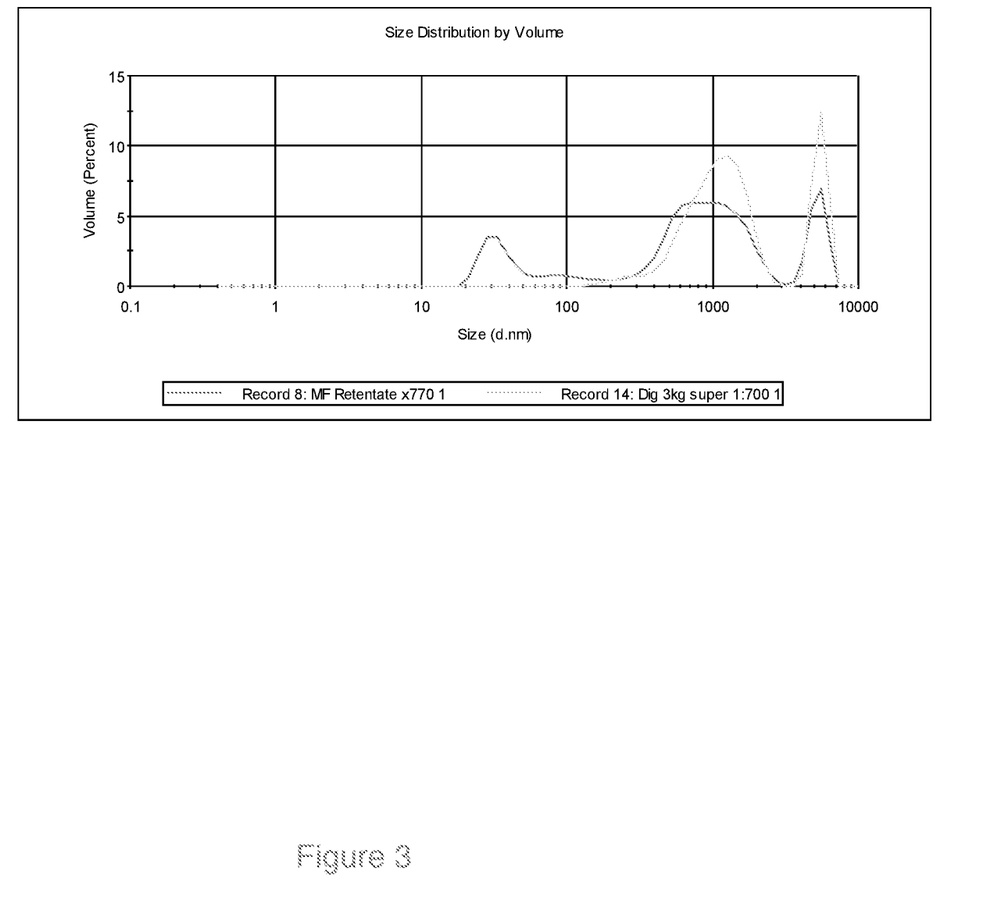
FIG. 3 shows particle size distribution for suspended solids in cow manure digestate liquid fraction and for steam pretreated wheat straw digestate liquid fraction.

A sample of simulated decanter liquid fraction from digestate of the anaerobic digestion of steam pretreated wheat straw pellets which is described in example 1 of WO2020/033633 was subject to microfiltration using a membrane having nominal exclusion 100 nm. Retentate from this microfiltration was used to compare with the simulated decanter liquid fraction from cow manure digestate referred to in example 1 in particle size determination analysis. Particle size determinations were made using a Malvern Zeta Sizer™ dynamic light scattering system. Scattering measurements were made as three separate tests recorded as means of 25 separate measurements. Although the replicates between the three tests showed some variability, the particle size distributions between the two samples were strikingly similar. FIG. 3 shows an overlay of particle size distribution measurements from each sample (red—dark, wheat straw liquid fraction microfiltration retentate at 1:770 dilution; green—light, simulated decanter liquid fraction from cow manure digestate at 1:700 dilution). As shown, particles sizes of suspended solids in digestate simulated decanter liquid fraction from both cow manure and steam pretreated wheat straw have a sharp peak centered around about 4000 nm in diameter, as determined in this experimental system. Both have a similar broad peak centered around a smaller size—about 1200 nm in the case of cow manure digestate liquid fraction, compared with about 900 nm in the case of steam pretreated wheat straw digestate.

4. Flocculation and Precipitation of Microparticles.

Figure 1:
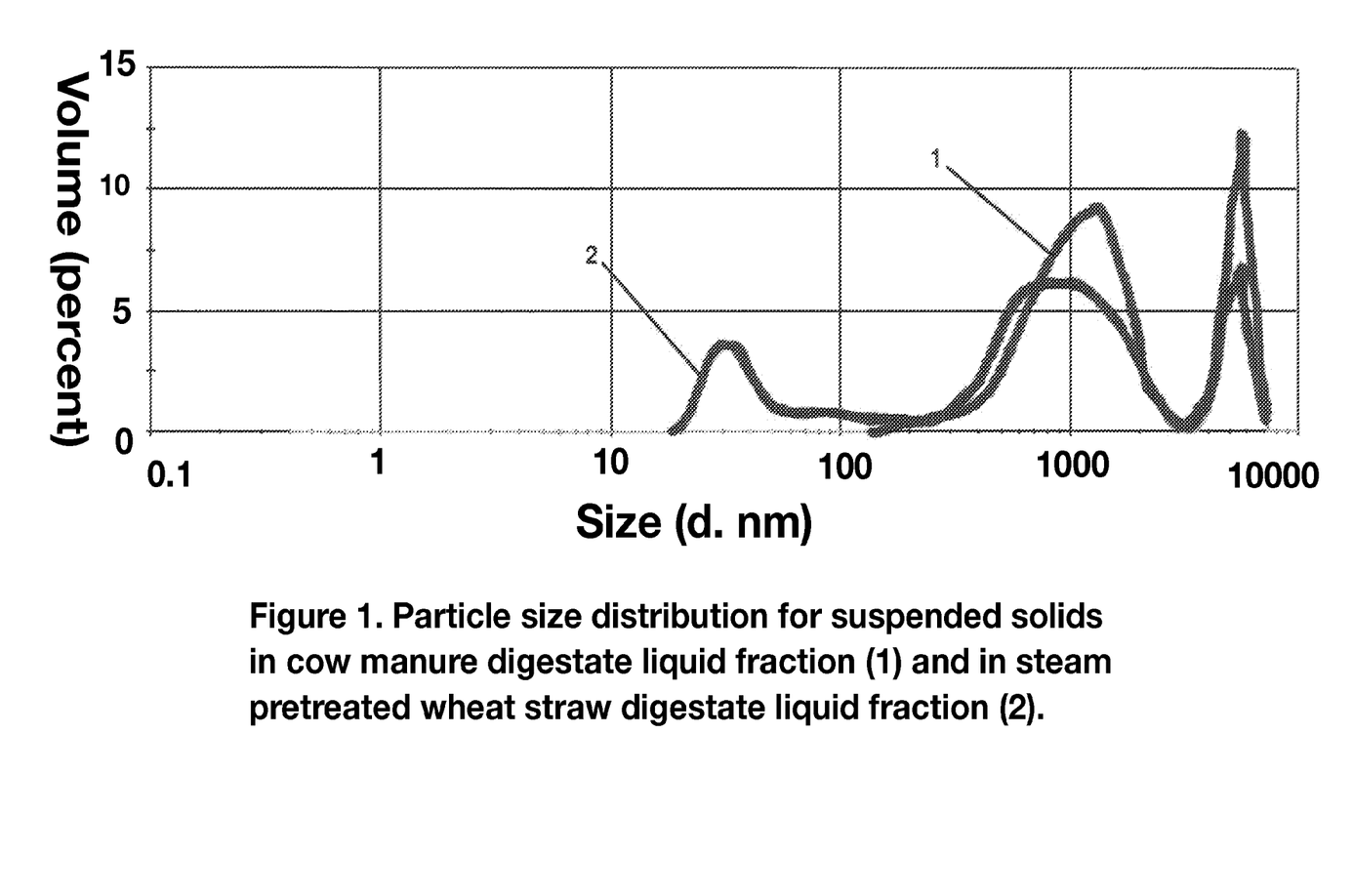
FIG. 1 shows cow manure digestate simulated decanter liquid fraction after adjustment to pH<2 followed by additional simulated decanter centrifugation.
Figure 2:
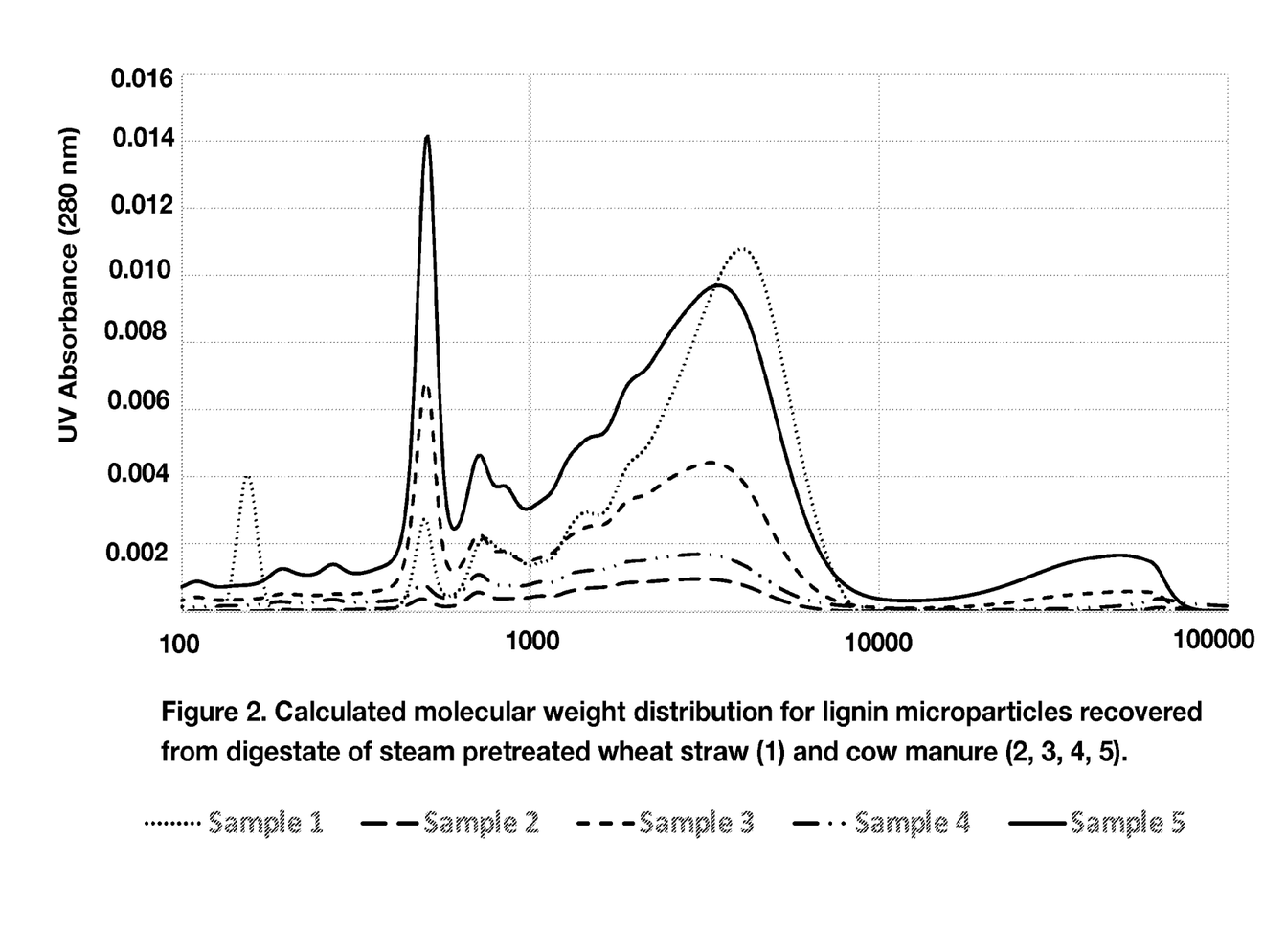
FIG. 2 shows supernatant from simulated decanter centrifugation of cow manure digestate liquid fraction with and without adjustment to pH<2.

The simulated decanter liquid fraction referred to in example 1 was used to observe behaviour of the material when pH was adjusted to <2. As explained in WO2020/033633, example 11, suspended lignin-rich microparticles from anaerobic digestion of steam pretreated wheat straw pellets can be flocculated and precipitated by adjusting pH<2. Samples of simulated decanter liquid fraction from cow manure digestate were introduced to 50 ml conical tubes, including one control in which pH was unadjusted, and two experimental in which pH was adjusted to <2 using concentrated sulfuric acid. After pH adjustment, the samples were allowed to sit one hour at room temperature, then centrifuged 5 minutes at 3600 g. FIG. 1 shows the appearance of the samples after pH adjustment and centrifugation. FIG. 2 shows the appearance of the supernatants after centrifugation from control pH 8 (bottom row of samples, appearing dark black) and experimental pH<2 (upper two rows of samples). As shown, the dark black particles were readily precipitated at pH<2, leaving a light blonde colored supernatant, exactly as described previously with microparticles from steam pretreated wheat straw digestate.

5. UV Absorbance of Dissolved Microparticles.

Figure 4:
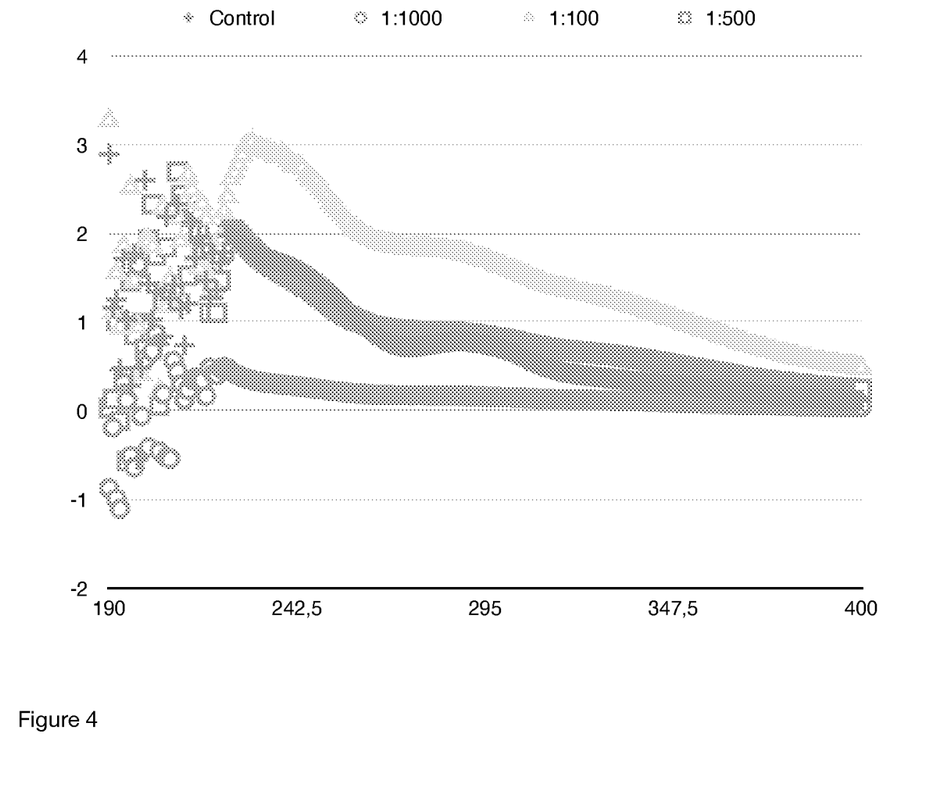
FIG. 4 shows the UV absorbance spectrum (190-400 nm) of a lignosulfonate standard compared with various dilutions of cow manure digestate liquid fraction adjusted to NaOH content 4 wt. %.

A sample of the simulated decanter liquid fraction referred to in example 1 was adjusted to pH 13 by adding NaOH to final 4 wt. %. UV absorbance spectra (190-400 nm) of the material was observed against a 1 N NaOH blank at three different dilutions in 1 N NaOH and compared with a lignosulfonate standard diluted 1:1000 in 1 N NaOH. Results are shown in FIG. 4—lignosulfonate standard (+symbols) and cow manure digestate liquid fraction with 4% NaOH (circles 1:1000, squares 1:500, triangles 1:100). As shown, the solubilized cow manure digestate liquid fraction solids exhibit UV absorbance similar to that of lignosulfonate standard.

6. Extraction of Digestate Solids Using 4% NaOH and Estimation of Lignin Recovery.

A sample of digestate solid fraction was obtained from Blūbjerg Biogas, Nørre Nebel, Denmark. The input feed to the digestion comprised approximately 85% cow manure. The digestate was processed on-site by screw press to produce a solid fraction and a liquid fraction. A sample of this solid fraction was dried overnight at 105° C. 36.8 g of dry matter (DM) from the dried solids was placed in a 500 ml blue cap bottle to which 220 g of a solution of 4 wt. % NaOH in water was added. The wetted sample was stored at 45° C. for 3 days. The wetted solids were subsequently distributed into 50 ml conical tubes (6 total) and centrifuged 2 hours at 3893 g. Supernatants were decanted and dry matter content determined as 9.2% (mean of N=2) using glass plates (avoiding reactions between aluminum and NaOH) and overnight drying at 105° C., corresponding to 5.2% extracted solids with 4% NaOH. The collected supernatants were concentrated by ultrafiltration using a membrane with nominal exclusion 1 Kd to final DM 18.6 wt. %. It will be readily understood by one skilled in the art that a similar technique for concentrating dissolved lignin can be applied using a liquid suspension of lignin-rich microparticles to which a sufficient quantity of sodium or potassium hydroxide has been added to dissolve the lignin content. Klason lignin content of the extracted material as determined by Celignis Laboratories, Limerick, was 46.4% by weight of the volatiles solids content of the extracted material. A total of 4.18 g lignin content was recovered from NaOH extraction of 36.8 g DM, indicating that the NaOH-extractable lignin content comprised about 11.4% of the digestate screw press solids DM. This estimate is consistent with the estimate shown in example 1 of 72.6% recovery of lignin content from cow manure digestate as a liquid suspension of lignin-rich microparticles after simulated decanter centrifugation: From an initial volatile solids content of 35.4 g/L, 40% was recovered as screw press solids of which 11.4% of DM was NaOH-extractable lignin content. This corresponds to 1.6 g/L NaOH-extractable lignin in screw press solids compared with 7.7 g/L (pellet volume loss corrected) recovered as lignin-rich microparticles in simulated decanter liquid fraction.

7. Molecular Weight Distribution of Lignin Microparticles from Digestate of Steam Pretreated Straw and of Cow Manure.

Figure 5:
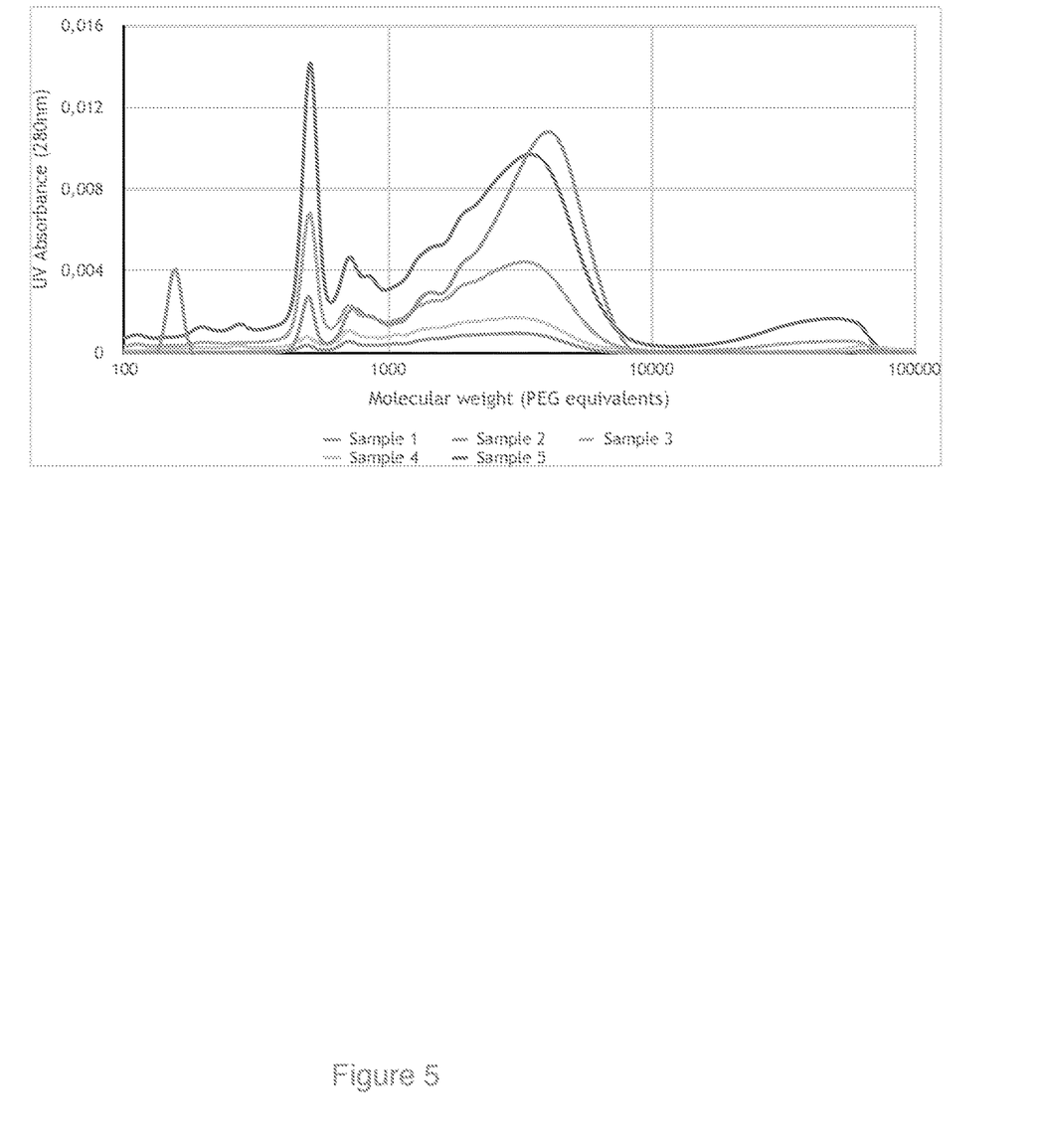
FIG. 5 shows the calculated molecular weight distribution for (sample 1) lignin microparticles recovered from steam pretreated wheat straw digestate liquid fraction compared with different dilutions of (samples 2 and 4) cow manure digestate simulated decanter liquid fraction and (samples 3 and 5) NaOH extract from cow manure digestate screw press solid fraction.

The sample described in example 17 of WO2020/033633 (suspended lignin-rich microparticles recovered from digestate of steam pretreated wheat straw pellets by flocculation of simulated decanter liquid fraction via adjustment to pH<2 which precipitated microparticles were subsequently dissolved by adding KOH to final wt. % 7.3) was used to compare with the concentrated NaOH extract of cow manure digestate solids described in example 6 and with the simulated decanter liquid fraction referred to in example 1 to which NaOH was added to 4 wt. %. The wheat straw digestate microlignin sample was diluted 1:450 in 0.1 N NaOH (sample 1). The cow manure simulated decanter liquid fraction sample was diluted 1:400 and 1:200 in 0.1 N NaOH (samples 2 and 4 respectively). The concentrated NaOH extract of cow manure solid fraction sample was diluted 1:400 and 1:200 in 0.1 N NaOH (sample 3 and 5 respectively). The samples were run on size exclusion chromatography (SEC) HPLC in 0.1 N NaOH along with polyethylene glycol molecular weight standards. Elution profiles were monitored using 280 nm absorbance. The calculated molecular weight distributions of each sample is shown in FIG. 5. The overlay of curves at the peak corresponding to molecular weight about 600 shows sample 5 uppermost, followed by sample 3, then sample 1, then sample 4, then sample 2 lowermost. As shown, the curves for samples 2 and 4 appear less intense simply because of the sample dilution applied and are otherwise virtually identical with the curves for samples 3 and 5. The curves for sample 3 and 5, having greater A280 intensity, clearly show a striking similarity with NaOH soluble material from wheat straw digestate microlignin. The steam pretreated straw digestate appears to lack the high molecular weight presumptive lignin observed in cow manure digestate, while possessing a low molecular weight component that is lacking in cow manure digestate. This is consistent with expectations that steam pretreatment at 190° C. as applied will cause some partial depoymerization of lignin content.

8. Determining Limiting NaOH Concentration at which Recovered Lignin Remains Soluble.

NaOH sufficient to make final wt. % 3.9 was added to the concentrated sample of simulated decanter liquid fraction from digestate of steam pretreated wheat straw pellets referred to in example 2. Aliquots from this sample were pipetted into Eppendorf™ tubes in triplicate then diluted to final NaOH concentration 70 mM, 50 mM, 40 mM and 30 mM. The tubes were centrifuged in a microfuge at 13.000 rpm for 20 minutes. Supernatants were decanted and wet pellet weight and pellet dry matter content were determined. Without correcting pellet dry matter for contribution from dissolved solids, dry pellet weights for each sample were expressed as a percentage of original DM added. At 70 mM and 50 mM NaOH, dry pellet weights corresponded to 15% or less of added DM. At 40 mM NaOH, however, >40% of added DM precipitated. This suggests that, to minimize process costs, solubilization can be achieved with tolerable losses using NaOH concentrations as low as 50 mM.

9. Valorization of Lignin Microparticles.

A sample of decanter or simulated decanter liquid fraction comprising at least 1 kg DM can be prepared from cow manure digestate screw press liquid fraction as described in example 1. NaOH sufficient to make final concentration 0.1 M can be added to the simulated decanter liquid fraction and lignin content thereby dissolved. The lignin solution can be concentrated by ultrafiltration to at least 20% volatile solids by weight of which at least 50% is Klason lignin content. NaOH can be added to the concentrated lignin solution sufficient to make final concentration 1.3 M. The concentrated lignin solution in 1.3 M NaOH can be subjected to alkaline oxidation at 160° C. for 30 minutes under 15 bar oxygen pressure as described in U.S. 62/984,302. The pH of reaction products can be adjusted to 7.0. Water soluble lignin oxidation products can thereafter be recovered and used as feed for anaerobic digestion to produce additional methane content.

The embodiments and examples described are exemplative only and not intended to limit the scope of the invention as defined by the claims.

ACKNOWLEDGMENTS

The support and advice of Prof. Ola Wallberg and Lund University Department of Chemical Engineering are gratefully acknowledged.

PATENT REFERENCES

WO2020/033633
WO2018/085487
U.S. 62/984,302

NON-PATENT REFERENCES

Abdelaziz, O. et al. "Oxidative Depolymerization of Kraft Lignin for Microbial Conversion," ACS Sustainable Chem. Eng. (2019) 7:11640-11652.

Donohoe, B. et al. "Visualising lignin coalescence and migration through maize cell walls following thermochemical pretreatment," Biotechnology and Bioengineering (2008) 101(5):913.

Guerra, A. et al. "Comparative Evaluation of Three Lignin Isolation Protocols for Various Wood Species," J. Agric. Food Chem. (2006) 54:9696-9705.

Hansen, M. et al. "Structural and chemical analysis of process residue from biochemical conversion of wheat straw (*Triticum aestivum* L.) to ethanol," Biomass and Bioenergy (2013) 56:572.

Ji, Z. et al. "Tissue specific response of *Miscanthus×giganteus* to dilute acid pretreatment for enhancing cellulose digestibility," Carbohydrate Polymers (2016) 154:247.

Li, H. et al. "Investigation of Lignin Deposition on Cellulose During Hydrothermal Pretreatment, Its Effect on Cellulose Hydrolysis, and Underlying Mechanisms," Biotechnology and Bioengineering (2014) 111(3):485.

Machtig, T. et al. "Anaerobic Biodegradability of Digestates—Influence of and Correlations for Klason lignin," Chem. Eng. Technol. (2020) 43:39.

Miranda, N. et al. "Meta-analysis of methane yields from anaerobic digestion of dairy cattle manure," Biomass and Bioenergy (2016) 86:65.

Mishra, P. and Ekielski, A. "The Self-Assembly of Lignin and Its Application in Nanoparticle Synthesis: A Short Review," Nanomaterials (2019) 9:243.

Pu, Y. et al. "Application of quantitative 31P NMR in biomass lignin and biofuel precursors characterization," Energy Environ. Sci. (2011) 4:3154.

Pu, Y. et al. "Assessing the molecular structure basis for biomass recalcitrance during dilute acid and hydrothermal pretreatments," Biotechnology for Biofuels (2013) 6:15.

Selig, M. et al. "Deposition of lignin droplets produced during dilute acid pretreatment of maize stems retards enzymatic hydrolysis of cellulose," Biotechnol. Prog. (2007) 23:1333.

Xiao, L. et al. "Impact of hot compressed water pretreatment on the structural changes of woody biomass for bioethanol production," BioResources (2011) 6(2):1576.

The invention claimed is:

1. A method for valorization of lignin-rich solids from anaerobic digestate comprising the steps of:
   conducting anaerobic digestion in a biogas plant on an input feed in which the predominant component is ruminant animal manure or in which the predominant components are lignocellulosic biomass and ruminant animal manure;

processing digestate from said anaerobic digestion by centrifugal or non-centrifugal means of solid/liquid separation so as to produce at least one solid fraction and at least one liquid fraction which at least one liquid fraction comprises Suspended lignin-rich microparticles;

processing the at least one liquid fraction comprising suspended lignin-rich microparticles so as to precipitate the suspended lignin-rich microparticles or so as to increase the concentration of suspended lignin-rich microparticles to at least 24 g/L to create a concentrated liquid suspension, or so as to dissolve the lignin content of the suspended lignin-rich microparticles in hydroxide solution, and processing the precipitated lignin microparticles or the concentrated liquid suspension or the hydroxide solution comprising dissolved lignin content so as to valorize the lignin content, wherein the lignocellulosic biomass digested in combination with ruminant animal manure has not been hydrothermally pretreated at temperature above the lignin melting point 130° C.

2. The method of claim 1 wherein the at least one liquid fraction is processed so as to increase the concentration of lignin-rich microparticles to between 40 and 110 g/L.

3. The method of claim 1 wherein the at least one liquid fraction processed so as to increase the concentration of suspended of lignin-rich microparticles to at least 24 g/L is valorized by catalytic thermal treatment using catalysts to produce higher value chemicals.

4. The method of claim 1 wherein the lignin content of the suspended lignin-rich microparticles is dissolved by addition of hydroxide base to make a lignin hydroxide solution.

5. The method of claim 4 wherein, if the processing the at least one liquid fraction is so as to dissolve the lignin content of the microparticles in hydroxide solution, the lignin content of the hydroxide solution is concentrated to between 24 and 300 g/L.

6. The method of claim 1 wherein, if the processing the at least one liquid fraction is so as to increase the concentration of the microparticles to at least 24 g/L to create a concentrated lignin suspension, the concentrated lignin suspension is valorized by alkaline oxidation to water soluble products which are subsequently subject to anaerobic digestion.

7. The method of claim 1 wherein the concentration of the suspended lignin microparticles in the at least one liquid fraction is increased by an initial concentration step followed by addition of hydroxide base to make a lignin hydroxide solution.

8. The method of claim 1 wherein, if the processing the at least one liquid fraction is so as to precipitate the suspended lignin-rich microparticles, the suspended lignin-rich microparticles are precipitated by lowering pH to <3 followed by either passive sedimentation or filtration.

9. The method of claim 8 wherein the lignin content of the precipitated lignin-rich microparticles is dissolved by addition of hydroxide base to form a lignin hydroxide solution.

10. The method of claim 1 wherein, if the processing the at least one liquid fraction is so as to dissolve the lignin content of the suspended lignin-rich microparticles in hydroxide solution, the lignin content of the hydroxide solution is concentrated to between 24 and 300 g/L.

11. The method of claim 10 wherein the lignin-concentrated hydroxide solution is valorized by alkaline oxidation to water soluble products which are subsequently subjected to anaerobic digestion.

12. The method of claim 1 wherein the at least one liquid fraction is produced by decanter centrifugation of digestate producing a solid fraction and a liquid fraction.

13. The method of claim 12 wherein the solid fraction is subsequently washed to recover additional lignin-rich microparticles.

14. A method for valorization of lignin from anaerobic digestate comprising the steps of:

conducting anaerobic digestion in a biogas plant on an input feed in which the predominant component is ruminant animal manure or in which the predominant components are lignocellulosic biomass and ruminant animal manure;

processing digestate from said anaerobic digestion by adding hydroxide base sufficient to dissolve lignin content of suspended lignin microparticles;

after hydroxide base treatment, processing the digestate from said anaerobic digestion by applying solid/liquid separation so as to produce at least one solid fraction and at least one liquid fraction comprising dissolved lignin; and processing the at least one liquid fraction so as to valorize its lignin content; and optionally subjecting the at least one solid fraction to additional anaerobic digestion.

15. The method of claim 14 wherein the lignin content of the processed at least one liquid fraction is concentrated in a subsequent step to between 24 and 300 g/L.

16. The method of claim 15 wherein the concentrated lignin at least one liquid fraction is valorized by alkaline oxidation to water soluble products which are subsequently subject to anaerobic digestion.

* * * * *